(12) United States Patent
Medow et al.

(10) Patent No.: US 12,350,456 B2
(45) Date of Patent: Jul. 8, 2025

(54) AUTOMATIC IN VITRO DIAGNOSTIC MEDICAL DEVICE FOR INTRAVENTRICULAR DRAINAGE

(71) Applicant: Wisconsin Alumni Research Foundation, Madison, WI (US)

(72) Inventors: Joshua Medow, Verona, WI (US); Yue Yang Mo, New Berlin, WI (US); Saketh Challa, Sharon, MA (US); Amber Rollette, Beloit, WI (US); Andrew Budde, Hartland, WI (US); Ronnie Alramahi, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 475 days.

(21) Appl. No.: 17/502,286

(22) Filed: Oct. 15, 2021

(65) Prior Publication Data
US 2023/0123678 A1   Apr. 20, 2023

(51) Int. Cl.
*A61M 27/00* (2006.01)
*A61M 39/28* (2006.01)

(52) U.S. Cl.
CPC ......... *A61M 27/006* (2013.01); *A61M 39/28* (2013.01); *A61M 2027/004* (2013.01); *A61M 2205/3344* (2013.01)

(58) Field of Classification Search
CPC ............... A61M 27/006; A61M 39/28; A61M 2027/004
See application file for complete search history.

(56) References Cited

U.S. PATENT DOCUMENTS

| | | | |
|---|---|---|---|
| 2003/0032915 A1* | 2/2003 | Saul | A61B 5/031 604/9 |
| 2008/0033400 A1* | 2/2008 | Holper | F04B 43/1253 600/561 |
| 2012/0302938 A1* | 11/2012 | Browd | A61M 39/284 604/9 |

(Continued)

FOREIGN PATENT DOCUMENTS

| | | | |
|---|---|---|---|
| DE | 102017001304 A | * | 8/2018 |
| DE | 102017001304 A1 | * | 8/2018 |
| WO | WO-2022076598 A1 | * | 4/2022 ........ A61M 27/006 |

OTHER PUBLICATIONS

Medtronic, Duet External Drainage and Monitoring System, Quick Reference Guide, 2009.

(Continued)

*Primary Examiner* — Susan S Su
*Assistant Examiner* — Erin A Kim
(74) *Attorney, Agent, or Firm* — Boyle Fredrickson SC (57) ABSTRACT

The present invention operates to significantly reduce over or under drainage of cerebrospinal fluid (CSF) from the brain or spinal cord using an extraventricular drain (EVD) in the brain or lumbar drainage device (LDD) and automated intracranial pressure (ICP) monitoring. The present invention attaches the drainage catheter of the EVD to a flow controller or valve which controls the flow of CSF from the drainage catheter and is electronically controlled by a stepper motor communicating with a pressure transducer receiving pressure signals indicating an ICP without the need for constant manual re-leveling.

16 Claims, 5 Drawing Sheets

(56) References Cited

U.S. PATENT DOCUMENTS

| | | | |
|---|---|---|---|
| 2016/0090262 A1* | 3/2016 | Wakayama | B65H 31/26 |
| | | | 271/223 |
| 2018/0055998 A1* | 3/2018 | Tu | A61M 27/006 |
| 2018/0228970 A1* | 8/2018 | Wostyn | A61K 9/0085 |
| 2018/0280670 A1* | 10/2018 | Iskandar | A61M 27/006 |
| 2019/0105476 A1* | 4/2019 | Turtz | A61B 5/0031 |
| 2021/0060315 A1* | 3/2021 | Golden | F16M 11/18 |

OTHER PUBLICATIONS

Moeller Medical GmbH, LiquoGuard CSF Drainage Pump Instruction Manual 2020.
https://www.lhsc.on.ca/critical-care-trauma-centre/procedure-setup-and-use-of-codman-eds-3-external-ventricular-drainage.
https://www.aesculapusa.com/en/healthcare-professionals/or-solutions/or-solutions-hydrocephalus/dualswitch-valve.html.

* cited by examiner

AUTOMATIC IN VITRO DIAGNOSTIC MEDICAL DEVICE FOR INTRAVENTRICULAR DRAINAGE

CROSS REFERENCE TO RELATED APPLICATIONS

STATEMENT REGARDING FEDERALLY SPONSORED RESEARCH OR DEVELOPMENT

BACKGROUND OF THE INVENTION

The present invention relates to neurosurgical devices used for treating patients with elevated intracranial pressure (ICP) and, more specifically, to an automated ICP management system that relieves pressure on the brain or spinal cord caused by excess cerebrospinal fluid (CSF) accumulation within the brain or spinal cord.

CSF is produced (approximately 500 to 600 mL/day) in the choroid plexuses of the ventricles of the brain and circulates through the ventricular system of the brain to the subarachnoid spaces in the cranium and spine to be absorbed into the bloodstream. The fluid is used to surround the brain and spinal cord and acts as a protective cushion or buffer against injury. It also contains nutrients and proteins for nourishment and functioning of the brain while clearing away waste products.

Hydrocephalus occurs when there is an imbalance between the amount of CSF that is produced and the amount that is absorbed resulting in an abnormal accumulation of cerebrospinal fluid (CSF) within the ventricles of the brain. Hydrocephalus may be caused by, for example, an intracranial hemorrhage, subarachnoid hemorrhage, cerebral edema, aneurysm, blood pooling in some part of the brain, traumatic brain injury, brain tumor, infections such as encephalitis or meningitis, high blood pressure, and stroke.

When CSF builds up within the brain, it causes the ventricles to enlarge and increases the pressure inside the skull and spinal cord. Elevated ICP (e.g., greater than 20 mmHg) is a dangerous condition which must be treated quickly to prevent further injury to the brain or spinal cord.

Elevated ICP can be treated through the placement of an extraventricular drain (EVD) within the brain to drain out extra CSF or blood from the brain. The EVD includes a drainage catheter installed between the brain's ventricles (i.e., lateral ventricle) or the subarachnoid space on one end and an attached collection bag on the other end through EVD tubing. Similarly, a lumbar drainage device (LDD) allows drainage from the lumbar subarachnoid space. A spinal needle, i.e., a Touhy needle, may be inserted into the lumbar subarachnoid space on one end and communicates through a spinal catheter which is attached to a collection bag outside the body on the other end.

In these drainage systems, the EVD tubing or spinal catheter are attached to a drip chamber which determines a pressure difference between a patient's ear (i.e., tragus) and a drip chamber height that is set to a desired patient ICP level. When the pressure through the EVD tubing or spinal catheter rises above the desired patient ICP level, CSF drains into the drip chamber, and when the pressure through the EVD tubing or spinal catheter is below the desired pressure level, CSF does not drain into the drip chamber. For example, if the drip chamber is positioned 10 mmHg above the patient's head, the ICP must be higher than 10 mmHg before drainage will occur. Lumbar CSF pressure is normally equal to the intracranial ICP.

A nurse is primarily responsible for monitoring drainage and manually releveling the drip chamber with respect to the patient's ear when the patient changes head position, and thus, the system requires close supervision and constant monitoring, usually at least every hour.

SUMMARY OF THE INVENTION

Physiological factors such as patient coughing, sneezing, vomiting, repositioning, physical exertion and the like can cause large, abrupt, spontaneous fluctuations in ICP which can trigger intervention, i.e., cerebrospinal fluid (CSF) drainage, that may not be indicative of a sustained increased (or decreased) ICP in the brain and therefore may result in over (or under) drainage of CSF. In some cases, greatly raised ICP conditions can also be caused by cerebral edema (i.e., severe brain swelling), not hydrocephalus, which may also cause drainage by the extraventricular drain (EVD) without excess CSF to drain resulting in empty or collapsed ventricles and congestion or occlusion of the drainage catheter (i.e., non-communicating hydrocephalus).

The present invention operates to significantly reduce over (or under) drainage of CSF from the brain using an EVD in the brain or lumbar drainage device in the spinal cord and automated ICP monitoring. The present invention attaches the drainage catheter of the EVD to a flow controller or valve which controls the flow of CSF from the drainage catheter and is electronically controlled by a stepper motor communicating with a pressure transducer and receiving pressure signals indicating an ICP within the brain to control drainage without the need for constant manual re-leveling. The valve may be automatically closed for brief amounts of time so that the ICP can be accurately sampled (e.g., at a rate of at least ten times the patient's heart rate) during drainage.

In one embodiment of the present invention, the valve may be a pinch valve or pinch roller type valve which compresses the EVD tubing to control the flow rate of CSF drainage from the brain or spinal cord. The pinch valve or pinch roller may stop CSF flow from the brain or spinal cord when the ICP falls into the desired range or trends toward a lower ICP (e.g., decreasing or monotonically decreasing), and may allow CSF flow from the brain or spinal cord when the ICP rises above the desired range or trends toward a higher ICP (e.g., increasing or monotonically increasing).

In one embodiment of the present invention, predetermined time delays may accommodate for abrupt changes or fluctuations in ICP by prohibiting changes to the drainage rate to take place until after the delay period has passed. Also, set tolerances may permit micro changes or tolerable changes of ICP to occur without automatically adjusting the drainage rate.

An upstream pressure transducer may indicate a pressure in the brain and a downstream pressure transducer may indicate a pressure below the brain in close proximity to the drainage bag. The change of pressure between the brain and a position near the drainage bag may assist with determining the drainage flow rate and can act as a flow rate sensor.

In one embodiment of the present invention, an inflatable/collapsible chamber or "balloon" chamber may be installed in-line with the EVD tubing in order to respond to greatly raised pressure increases which may indicate critical pressures signifying swelling in the brain without CSF drainage. When critical pressures are detected, drainage is immediately stopped therefore preventing over-drainage of CSF and allowing for alternative medical intervention to be performed. For example, a computed tomography (CT) scan of the brain may be used to confirm if cerebral edema is present.

Specifically, in one embodiment, the present invention provides a cerebrospinal fluid (CSF) drainage system used to treat an abnormal accumulation of CSF in a brain or spinal cord of a patient. A medical tubing is connectable to a catheter implanted within the brain or spinal cord of the patient with a proximal portion of the catheter within the brain or spinal cord opposite a distal portion of the catheter attachable to the medical tubing and configured to divert CSF out of the brain or spinal cord to the external medical tubing. A pressure sensor is connectable to the medical tubing and is configured to produce a signal representing an intracranial pressure. A valve is positioned downstream from the pressure sensor and is connectable to the medical tubing to conduct excess CSF through the medical tubing in an open position and to prevent the excess CSF from passing through the medical tubing in a closed position. A valve driver control circuit communicates with the pressor sensor and the valve and operates to receive the signal representing the intracranial pressure and to control the valve to (a) switch the valve between the open and closed position at a first rate as a function of intracranial pressure and (b) switch the valve between the open and closed position at a second rate independent of intracranial pressure, where the second rate is higher than the first rate.

It is thus a feature of at least one embodiment of the invention to electrically control operation of an external valve according to measured ICP of an EVD system to permit sophisticated control of the valve and allow for "simultaneous" ICP measurement and drainage operation. A micro sensor does not need to be implanted within the brain or spinal cord.

The second rate may be at least ten times the average heart rate of a human patient. The second rate may be at least 10 times per second. The second rate may be at least 15 times per second.

It is thus a feature of at least one embodiment of the invention to permit ICP monitoring without manually shutting off the stopcock to the drainage bag that can be accomplished at a much higher sampling rate allowing for much more precise flow control management.

The valve driver may be adapted to open the valve when the signals representing the intracranial pressure are above a predetermined threshold for a predetermined duration at least 2 seconds representing a sustained high intracranial pressure. The predetermined duration may be between 2 and 5 seconds.

It is thus a feature of at least one embodiment of the invention to reduce intervention and over drainage during transient changes in ICP representative of physical movement, such as a cough or sneeze, but not indicating a sustained elevated ICP.

The valve driver may be adapted to open the valve for signals representing an average intracranial pressure that is increasing monotonically.

It is thus a feature of at least one embodiment of the invention to provide anticipatory monitoring that provides early and less intense intervention reducing over treatment and "overshooting."

The valve driver control circuit may be configured to regulate a valve position with respect to the medical tubing. The flow rate may be adjusted by changing a cross sectional area of the medical tubing.

It is thus a feature of at least one embodiment of the invention to provide a non-invasive "passive" method of regulating flow through the medical tubing by restricting gravity influenced flow through the medical tubing rather than "active" pumping actively moving the fluid through the tubing.

The valve may be a pinch valve pinching an outer surface of the medical tubing. The pinch valve may be a roller rollable along the medical tube to compress the medical tubing.

It is thus a feature of at least one embodiment of the invention to quickly move the valve between open and closed positions with high accuracy and safety.

The roller may compress the medical tubing in a first position and decompress the medical tubing in a second position wherein the first and second positions are approximately 90 degrees apart.

It is thus a feature of at least one embodiment of the invention to allow for closing rotation to be opposite the direction of fluid flow through the tubing thus reducing the amount of additional CSF drainage (i.e., over drainage) upon valve closure.

The valve may include a position sensor detecting a position of the roller between the first position and the second position. The valve may further comprise stop blocks preventing rotation of the roller beyond the 90 degree rotation.

It is thus a feature of at least one embodiment of the invention to provide safeguards and absolute limits ensuring proper placement and position detection of the roller.

A second pressure sensor may be connected to the medical tubing downstream from the valve and produces a signal representing a pressure at a position below the brain of the patient.

It is thus a feature of at least one embodiment of the invention to utilize a downstream pressure sensor permitting for flow rate detection and drainage rates which can be used in closed loop systems to control flow.

An expandable chamber may be connected to the medical tubing and may be configured to expand with high intracranial pressure and produce a signal to the valve to close the valve. A photo sensor may detect a change in light level as the expandable chamber expands indicating high intracranial pressure.

It is thus a feature of at least one embodiment of the invention to detect extreme rises in ICP indicating possible swelling in the brain with minimal CSF drainage and when further drainage should stop.

The present invention also provides a method of treating hydrocephalus where there is an abnormal accumulation of cerebrospinal fluid (CSF) in a brain or spinal cord of a patient. The method includes the steps of connecting a proximal end of medical tubing to a catheter implanted within the brain or spinal cord of the patient with a proximal portion of the catheter within the brain or spinal cord opposite a distal portion of the catheter attachable to the medical tubing and diverting CSF out of the brain or spinal cord to the medical tubing. The medical tube is connected to a pressure sensor producing a signal representing an intracranial pressure when the valve is in the closed position; a valve downstream from the pressure sensor to conduct excess CSF to drain out of the brain or spinal cord through the medical tubing in an open position and to prevent the excess CSF from passing out of the brain or spinal cord through the medical tubing in a closed position; and a valve driver control circuit communicating with the pressor sensor and the valve and operating to receive the signal representing the intracranial pressure and to control the valve to switch the valve between the open position and closed position and (a) switch the valve between the open and closed position at a first rate as a function of intracranial pressure and (b) switch the valve between the open and closed position at a second rate independent of intracranial pressure, where the second rate is higher than the first rate.

These particular objects and advantages may apply to only some embodiments falling within the claims and thus do not define the scope of the invention.

DETAILED DESCRIPTION OF THE PREFERRED EMBODIMENT

Figure 1:
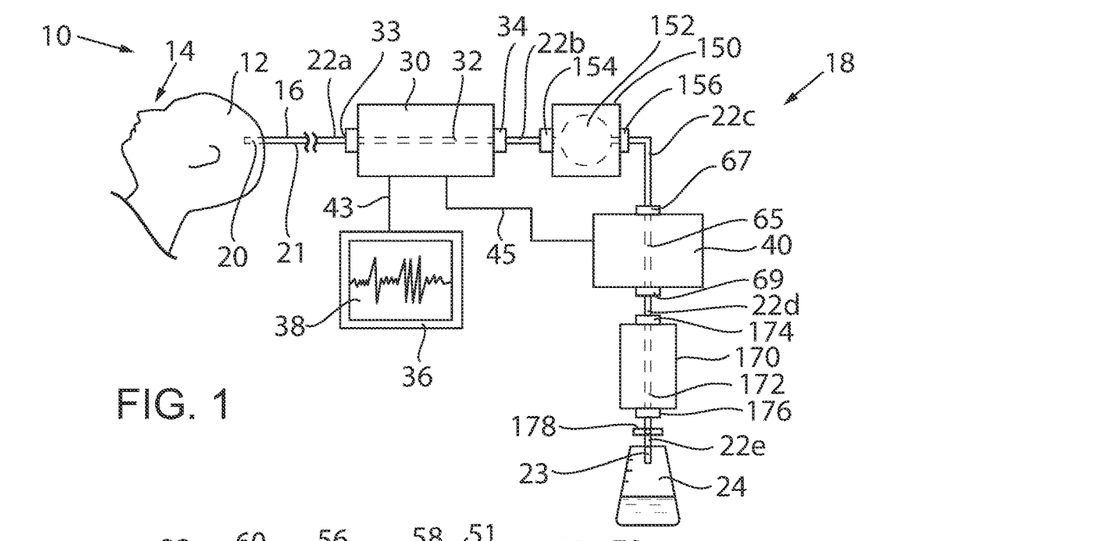
FIG. 1 is a schematic of an automated cerebrospinal fluid (CSF) management system of one embodiment of the present invention showing an extraventricular drain (EVD) installed within a patient's brain and attached to a pressure transducer, the pressure transducer further attached to a monitor, collapsible chamber, and flow controller, the flow controller regulating flow to a second pressure transducer and drainage bag.

Referring to FIG. 1, an extraventricular drain (EVD) 10 of the present invention may be inserted within a head 12 of a human patient 14. The human patient 14 may be in a supine position with the head 12 of the human patient 14 elevated between 30 to 60 degrees and at an approximately 45 degrees incline.

In one embodiment of the present invention, a burr hole is placed at the human patient's Kocher's point. A linear skin incision is made down to the bone and the periosteum is scraped. A twist drill is used to penetrate the cranium and the pia and dura pierced with a scalpel. A drainage catheter 16 is inserted in a coronal plane toward the medical canthus of the ipsilateral eye and in the anteroposterior plane toward a point 1.5 cm anterior to the ipsilateral tragus, toward the ipsilateral Foramen of Monro to commence cerebrospinal fluid (CSF) flow through the drainage catheter 16. The drainage catheter 16 is tunneled through the skin at a separate incision, sutured securely in place, and connected to an external drainage system 18.

The drainage catheter 16 may alternatively be surgically implanted in the spine to approach the ventricle or other CSF space where CSF resides so that CSF may be drained from the patient's brain or spinal canal.

A proximal end 20 of the drainage catheter 16 may be closed at the tip but may include several small drainage holes allowing the CSF to flow from the ventricles or subarachnoid space through the holes and into the drainage catheter 16. A distal end 21 of the drainage catheter 16 may be attached to the external drainage system 18.

The drainage catheter 16 may be of the type described in U.S. Pat. No. 10,709,879, entitled "Cerebrospinal-fluid Shunt Valve System," hereby incorporated by reference and assigned to the present applicant.

Although the drainage catheter 16 is being shown and described as installed within the head 12 of the human patient 14, a proximal end 20 of the drainage catheter 16 may also be installed within the subarachnoid space in the spinal cord of the human patient 14, as understood in the art, and a distal end 21 of the drainage catheter 16 may be attached to the external drainage system 18 in a similar manner as described below.

The external drainage system 18 fluidly communicates with the drainage catheter 16 to obtain a fluid pressure representative of the intracranial pressure (ICP) and manages the ICP through an adjustable drainage of the CSF from the brain's ventricles or subarachnoid space or spinal cord to an external location such as a drainage bag 24. The external drainage system 18 may include a medical tubing 22 connectable to the drainage catheter 16, for example, by a Luer lock connector, the medical tubing 22 further communicating with the drainage bag 24 at a distal end of the medical tubing 22 to allow for drainage of CSF into the drainage bag 24, relieving elevated ICP within the brain. The medical tubing 22 may be an IV line, e.g., 3.5 mm diameter IV line, made from polyvinyl chloride (PVC), polyethylene, or polypropylene plastic, and may be softened with plasticizers making it more flexible. The IV line may be a highly compliant material that may be sterilizable and is, preferably, non-Pyrogenic, non-DEHP and latex-free.

An upstream pressure transducer 30 may be installed on the medical tubing 22 and may fluidly communicate with the medical tubing 22 using a medical tubing 22 integrated with a non-compliant pressure tubing section 32 or using a short section of non-compliant pressure tubing section 32 attached to the medical tubing 22 using connectors 33, 34, for example, Luer lock connectors. In the latter, a first portion of the medical tubing 22a is connected to a first connector 33 of the pressure transducer 30 and a second portion of the medical tubing 22b may be attached to a second connector 34 of the pressure transducer 30 to provide a leak proof union between the medical tubing 22 and the non-compliant pressure tubing section 32. The non-compliant pressure tubing section 32 may be used within the pressure transducer 30 to ensure consistent and accurate pressure measurement.

Generally, the pressure transducer 30 will convert an applied pressure of the CSF flow through the non-compliant pressure tubing section 32 into an electrical signal to provide ICP data to a bedside monitor 36 and a flow controller 40, as further described below. The non-compliant pressure tubing section 32 deforms under the application of pressure caused by the CSF flow and this deformation is detected to provide a pressure reading representative of the ICP (i.e., the ICP data). In order to obtain an accurate pressure reading of the ICP, drainage through the medical tubing 22 is blocked while the pressure measurement is being taken, as further discussed below.

The pressure transducer 30 may be of the type sold by ICU Medical of San Clemente, CA, under the commercial product name "Transpac IV Disposable Pressure Transducer."

The position of the pressure transducer 30 is preferably fixed with respect to the head 12 of the human patient 14 so that the pressure transducer 30 moves with respect to the head 12 of the human patient 14 and is preferably in line with or close to the Foramen of Monro which falls at the level of the external auditory meatus of the ear in the supine position. The pressure transducer 30 may be attached to the head 12 of the human patient 14, for example, using medical tape, bandage, adhesive, or the like.

The pressure transducer 30 may include an output connector 43 allowing it to be electronically connected to a bedside monitor 36 for displaying the ICP data from the pressure transducer 30 and that can be viewed instantaneously by the medical professional during monitoring and management of the ICP. The bedside monitor 36 may provide a display screen 38 and buttons, or a touch screen, allowing the medical professional to set up the monitor and change settings on the monitor. The bedside monitor 36 may also communicate with a hospital network allowing ICP data from the pressure transducer 30 to be stored in an electronic medical record (EMR) system that can be retrieved and reviewed later. The output connector 43 may be a "telephone style" or RJ11 cable connector that is connectable to conventional bedside monitors 36.

The bedside monitor 36 may be of the type sold by Philips North America Corporation of Cambridge, MA.

The pressure transducer 30 may further include an output connector 45 allowing it to be electronically connected to a flow controller 40 which responds to the ICP data from the pressure transducer 30 to open, partially close, and fully close a valve 41 of the flow controller 40 to regulate the drainage rate through the flow controller 40. The output connector 45 may be a "telephone style" or RJ11 cable connector that is connectable to the flow controller 40.

Fluid flows through the pressure transducer 30 and then, optionally, through a high pressure detector 150 joined to the second portion of the medical tubing 22b and a third portion of the medical tubing 22c at opposite ends of the high pressure detector 150 to detect greatly raised pressures, as described in further detail below with respect to FIG. 10.

Figure 2:
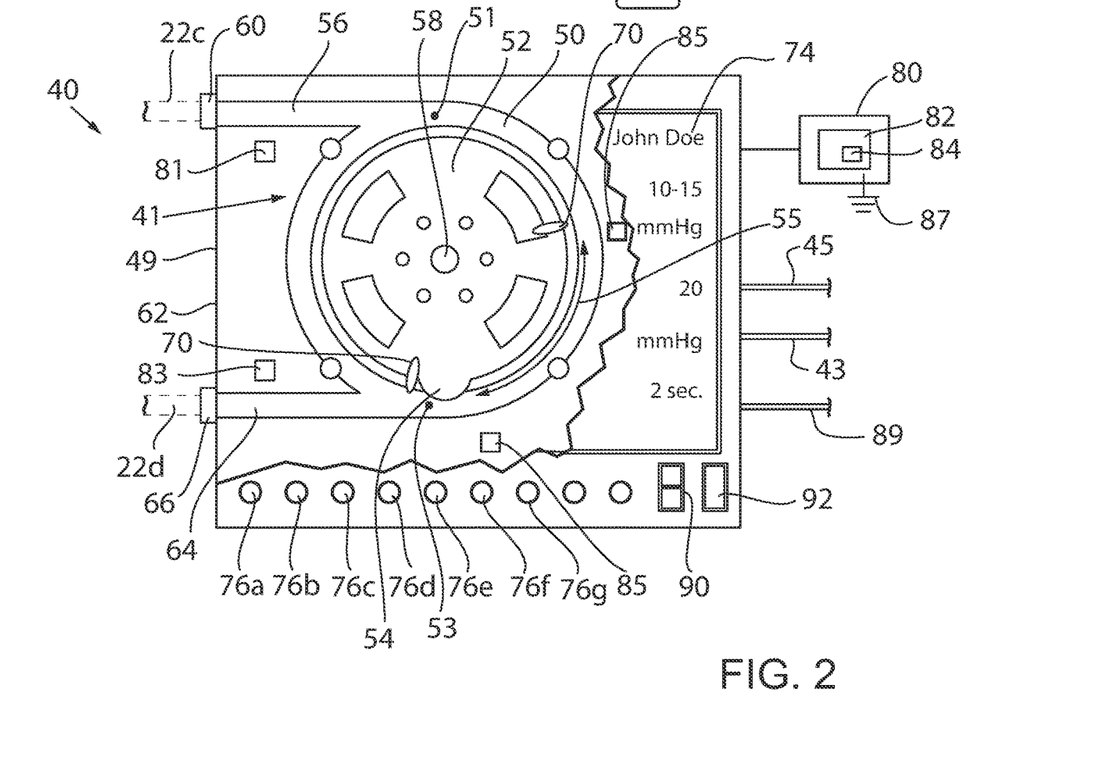
FIG. 2 is a flow controller of the automated CSF management system of FIG. 1 providing a valve that is a rotating guide rotating a roller 90 degrees back and forth to compress the EVD tubing in a closed position and decompress the EVD tubing in an open position.

Referring now to FIG. 2, a flow controller 40 will fluidly receive the third portion of the medical tubing 22c from the high pressure detector 150 to receive the CSF flow. The flow controller 40 may include a valve housing 49 being generally a rectangular enclosure carrying a circular channel 50 receiving the medical tubing 22 therein and further supporting a valve 41 compressing the outside of the medical tubing 22. The valve 41 may be entirely external to the medical tubing 22 so that the valve 41 does not directly contact the CSF or inner lumen of the medical tubing 22 and therefore isolates the CSF from external contamination. The valve 41 compresses and directly contacts only the outer surface of the medical tubing 22 to selectively permit or limit the flow through the medical tubing 22. In this respect the flow controller 40 may be reused and is not contaminated by the CSF. The flow controller 40 is generally positioned at or below the level of the patient's ear (i.e., tragus).

Rolling Pinch Valve

According to one embodiment of the present invention, the valve 41 of the flow controller 40 may be a rolling pinch valve, as shown in FIG. 2, having a circular channel 50 receiving the medical tubing 22 therein. A rotating guide 52 supporting an outwardly extending roller 54 can rotate with respect to the circular channel 50 to slide the outwardly extending roller 54 along the circular channel 50 to selectively compress the medical tubing 22 held within the circular channel 50.

The circular channel 50 of the valve housing 49 may include an inlet channel 56 extending from an inlet opening 60 in a left side wall 62 of the valve housing 49 and into a top end of the circular channel 50 allowing the medical tubing 22 to be inserted from outside the valve housing 49 into the circular channel 50. The medical tubing 22 follows a generally straight path of the inlet channel 56 to a circular path of the circular channel 50. The medical tubing 22 may further follow the circular path of the circular channel 50 to an outlet channel 64 extending from a bottom end of the circular channel 50 to an outlet opening 66 in the side wall 62 of the valve housing 49 allowing the medical tubing 22 to extend from the circular channel 50 into the generally straight path of the outlet opening 66 to an outside of the valve housing 49.

The circular channel 50, inlet channel 56, and outlet channel 64 may snugly receive the medical tubing 22 therein, the cross sectional diameter of the circular channel 50 being approximately the same or slightly larger than the outer diameter of the medical tubing 22, for example, between 3.5 mm to 4.0 mm.

The inlet channel 56 and outlet channel 64 are substantially parallel channels extending through the left side wall 62 of the valve housing 49 and receiving the medical tubing 22 therein. The inlet channel 56 and outlet channel 64 are substantially tangential to a top and bottom end, respectively, of the circular channel 50 such that the inner walls of the inlet channel 56 and outlet channel 64, respectively, are tangential to an outer diameter of the circular channel 50. Therefore, the inlet channel 56 and outlet channel 64 create a larger diameter channel at the tangent points 51, 53 at the top and bottom, respectively, of the circular channel 50 allowing the outwardly extending roller 54 to extend into the circular channel without compressing the medical tubing 22. The diameter of the channel at the tangent points 51, 53 may be, for example, approximately twice or at least twice the diameter of the circular channel 50, the outer diameter of the medical tubing 22, and the extension distance of the protruding roller 54. The diameter of the channel at the tangent points 51, 53 may be, for example, between 7 mm to 8 mm.

It is understood that inlet channel 56 and outlet channel 64 may extend in any direction, for example, up, down, left or right from the circular channel 50, allowing the medical tubing 22 to be inserted through and extend from any wall of the valve housing 49, for example, a top wall, left side wall, right side wall or bottom wall of the valve housing 49.

The rotating guide 52 of the valve 41 may be a circular wheel positioned inside the circular channel 50 and generally centered therein to rotate about a center axis 58 and supporting a protruding roller 54 which extends outwardly from the rotating guide 52 into the circular channel 50 to extend substantially across the width of the circular channel 50. The extension distance of the protruding roller 54 into the circular channel 50 is approximately equal to the cross sectional diameter of the circular channel 50. For example, the protruding roller 54 may extend between 3.5 mm to 4.0 mm across the circular channel 50.

The rotating guide 52 and the protruding roller 54 are permitted to rotate approximately 90 degrees, as shown by arrow 55, between two physical blocks 70, which prevent further movement of the protruding roller 54 beyond the 90 degree rotation.

In a first, "off" position, the protruding roller 54 extends across the circular channel 50 at a "3 o'clock" position to fully compress the medical tubing 22 and occlude the medical tubing 11 installed within the circular channel 50. When the valve 41 is in the first "off" position, CSF is blocked from flowing through the valve 41.

In a second "on" position, the protruding roller 54 extends across the circular channel 50 at the tangential point 53 of the circular channel 50, or at a "6 o'clock" position, allowing the medical tubing 22 to pass from the circular channel 50 into the outlet channel 64 without being compressed. Alternatively, the protruding roller 54 could extend across the circular channel 50 at the tangential point 51 of the circular channel 50, or at a "12 o'clock" position, allowing the medical tubing 22 to pass from the inlet channel 56 into the circular channel 50 without being compressed. In this respect, the protruding roller 54 does not compress the medical tubing 22 in the "on" position because it bypasses the protruding roller 54. When the valve 41 is in the second "on" position, CSF is allowed to drain through the valve 41.

It may be desired to move the protruding roller 54 counterclockwise (i.e., from the "6 o'clock" to "3 o'clock" position), against the flow direction of CSF, when moving from the second "on" position to the first "off" position in order to minimize the amount of CSF allowed to drain through the valve 41 upon valve closing. Likewise, it may be desired to move the protruding roller 54 clockwise (i.e., from the "3 o'clock" to "6 o'clock" position), in the same flow direction as the CSF, when moving from the first "off" position to the second "on" position to permit CSF to drain through the valve 41 upon valve opening.

The rotating guide 52 may rotate to move the protruding roller 54 between the first "off" position and the second "on" position in order to open and close the valve 41 at a rapid pace for frequent pressure readings. In order to obtain accurate pressure readings at the pressure transducer 30, drainage through the valve 41 should be turned "off" enabling a "true" ICP reading from the patient (otherwise the drainage pressure will also be obtained). In this respect, CSF drainage and ICP measurements cannot be measured at the exact same time and the valve 41 must be turned off for a short amount of time to take an accurate pressure reading. Upon turning the valve 41 "off," the ICP reading may be allowed to stabilize for a brief amount of time prior to taking the ICP reading.

It is understood that a softer silicone rubber section 65 may be used within the flow controller 40. For example, the third portion of the medical tubing 22c may be connected to a first connector 67 of the flow controller 40 and a fourth portion of the medical tubing 22d may be attached to a second connector 69 to provide a leak proof union between the medical tubing 22 and the flow controller 40. The first and second connectors 67, 69, which may be Luer lock connectors, joined respectively to ends of the central softer silicone rubber section 65 which may be used within the flow controller 40 to allow the softer silicone rubber section 65 to be resiliently compressed without breakage. Alternatively, the flow controller 40 may provide a protective resilient sleeve wrapped around the medical tubing 22 to strengthen and protect the medical tubing 22 from breakage with repeated compressions. The sleeve may be made of silicone rubber.

Figure 3:
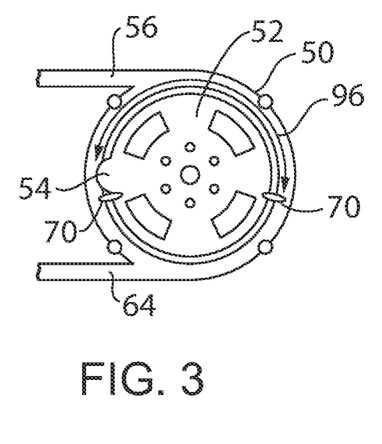
FIG. 3 is an alternative embodiment of the valve of FIG. 2 providing a rotating guide rotating a roller 180 degrees back and forth to compress the EVD tubing in a closed position and decompress the EVD tubing in an open position.

Other variations of the rolling pinch valve 41 are contemplated by the present invention. Referring to FIG. 3, in an alternative embodiment of the invention, the rotating guide 52 and the protruding roller 54 may rotate approximately 180-degrees back and forth on an upper half of the circular channel 50 as indicated by arrow 96, between two physical blocks 70, to move the protruding roller 54 to a first "off" position where it extends across the circular channel 50 at a "3 o'clock" position at a right side of the circular channel 50 to compress the medical tubing 22 closed, and a second "on" position where it extends across the circular channel 50 at a "9 o'clock" position at a left side of the circular channel 50 that does not hold the medical tubing 22 and therefore does not compress the medical tubing 22. It is understood that the rotating guide 52 and the protruding roller 54 may rotate approximately 180-degrees back and forth along a lower half of the circular channel 50 in a similar manner.

Figure 4:
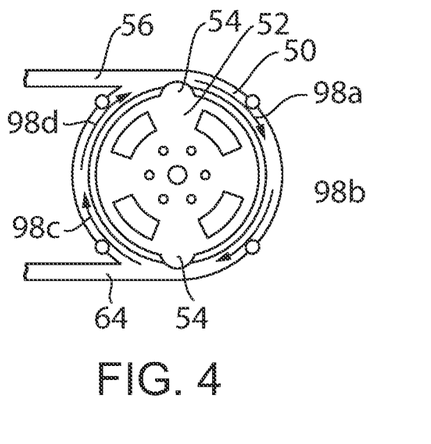
FIG. 4 is an alternative embodiment of the valve of FIG. 2 providing a rotating guide rotating a roller 360 degrees in 90 degree increments in one direction to compress the EVD tubing in a closed position and decompress the EVD tubing in an open position.

Referring to FIG. 4, in an alternative embodiment of the invention, the rotating guide 52 may rotate a pair of oppositely positioned protruding rollers 54 to rotate 360-degrees, in one direction clockwise or counterclockwise, in 90-degree cycles as indicated by separate cycle arrows 98a, 98b, 98c, 98d, to move the pair of oppositely positioned protruding rollers 54 to a first "off" position where the rollers 54 extend across the circular channel 50 at opposed "3 o'clock" and "9 o'clock" positions at a left and right side of the circular channel 50 so that at least one protruding roller 54 compresses the medical tubing 22 closed, as seen by arrows 98a and 98c, and to a second "on" position where the rollers 54 extend across the circular channel 50 at opposed "12 o'clock" and "6 o'clock" positions at a top and bottom of the circular channel 50, as seen by arrows 98b and 98d, which allow the medical tubing 22 to extend from and into the inlet channel 56 and outlet channel 64 bypassing the rollers 54 without being compressed, similar to the clearance provided by the rolling pinch valve 41 of FIG. 2.

Other known fluid valves 41 are compatible with the present invention and may include other forms of pinch valves which compress an outside of the tube to alter the fluid opening of the medical tubing 22 between open and close, and various positions in between, and to regulate the flow rate through the flow controller 40. Other known types of valves 41 (and variable flow rate valves, for example, as described below with respect to FIGS. 7 and 8) include stopcocks, tube crimps, linear actuators, magnetic actuators, and the like, which may be automatically electronically operated dependent on ICP signals received by the flow controller 40.

Referring again to FIG. 2, the valve housing 49 of the flow controller 40 may further present on its front face a user interface 74 comprising, for example, a liquid crystal type display 75 for displaying symbols and alphanumeric characters under computer control or a more advanced touchscreen display 75 may be used for inputting and displaying information. The user interface 74 also provides multiple membrane switch pushbuttons 76 that may be activated by a user. Alternatively, the pushbuttons 76 may be virtual buttons shown on the touchscreen display 75.

Generally, the pushbuttons 76 include a limited number of controls including, in one embodiment, menu 76a, zero 76b, error/clear 76c, up 76d, down 76e, enter 76f, and reset 76g buttons. For example, the menu button 76a will be pressed to initiate a calibration sequence and the zero button 76b will be pressed during the calibration sequence of the flow controller 40 to store a calibration pressure set to an atmospheric pressure (around 760 mmHg) when the pressure transducer 30 is exposed to air in the room and the atmospheric pressure readings have stabilized. The up button 76d, down button 76e, and enter button 76f will be pressed to allow the user to set a target pressure range of the ICP, e.g., within a healthy range of about 10 to 15 mmHg. The error/clear button 76c will be pressed to clear the screen or return to a previous screen and the reset button 76g is used to restore the flow controller 40 to factory settings.

The valve housing 49 of the flow controller 40 may include a microcontroller 80 being an electronic computer having a self-contained nonvolatile memory 82 holding an operating program 84 and necessary storage variables. The nonvolatile memory may comprise, for example, flash memory and/or read only memory, or other similar nonvolatile memory as context requires, which may store data values to be retained even in the absence of electrical power.

The microcontroller 80 also provides various inputs and output lines communicating, for example, with the display 75 for providing display information thereon and the various pushbuttons 76 for receiving data related to their activation by user. In addition, the microcontroller 80 may provide control lines to the rotating guide 52 and roller 54 having, for example, an internal DC electric motor (not shown) operating through a gear system to activate rotation of the rotating guide 52 and roller 54 that may press against the medical tubing 22 to stop or slow fluid therethrough.

The microcontroller 80 may also communicate electrically with various sensors. For example, upstream and downstream pressure sensors 81, 83 which can be used to ensure proper operation of the valve 41 by detecting abnormal pressures which may indicated a blockage or leak. Proximity or photosensors 85 can be used to ensure proper positioning of the protruding roller 54 which ensures proper placement of the protruding roller 54 in the "on" and "off" positions or positions in between. Additional proximity, photosensors, or mechanical sensors (not shown) can be used to obtain flow rate readings and medical tubing orifice size which ensure proper CSF flow and drainage. Abnormal readings may cause an alert or indication to be provided to the medical professional, for example, an audio alarm, visual display or other computer-controlled activation (motor buzz, etc.).

All electrical components in the flow controller 40 may be supplied with power by a contained storage battery 87 that may provide its power directly or through standard power processing circuits such as regulators and the like. Alternatively, an AC mains power source may supply power through a line cord 89. A loss of the power from the AC mains power source or a low battery may cause an alert or indication to be provided to the medical professional, for example, an audio alarm, visual display or other computer-controlled activation (motor buzz, etc.). An on/off switch 90 on the valve housing 49 will turn power to the electrical components on and off.

The microcontroller may communicate with the contained storage battery 87 and a charging circuit communicating with a USB jack 92 for external charging through a wall of the valve housing 49. The USB jack 92 may also be used to allow ICP data to be transferred to an external storage device, e.g., an external thumb drive or external storage device, for further downloading to a computer and retrieval of ICP data.

Valve Control Circuit

Figure 5:
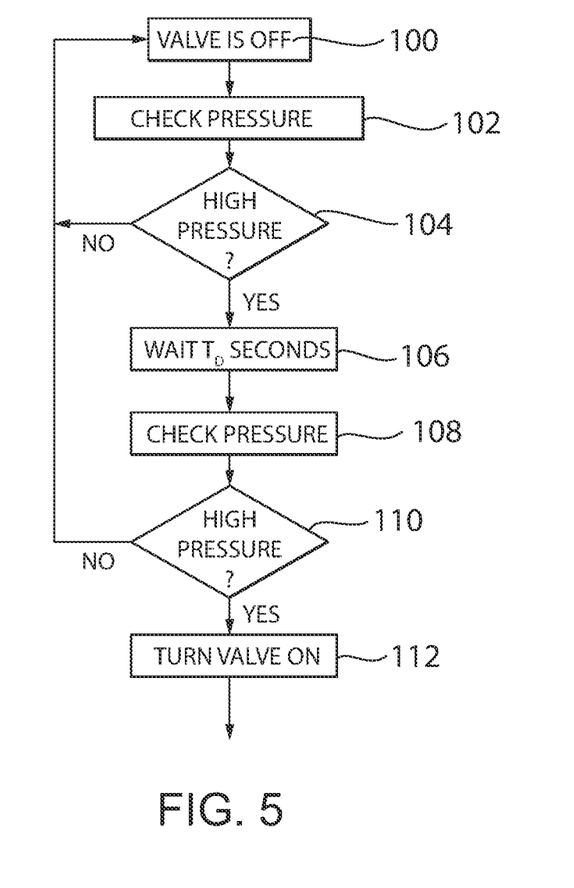
FIG. 5 is a flow diagram showing closed valve operation of the flow controller of FIGS. 1 and 2 to accommodate for transient changes or fluctuations in intracranial pressure (ICP) caused by coughs or sneezes and to check for ICP at a high sampling rate.

Referring to FIG. 5, the microcontroller 80 may run the operating program 84 stored in self-contained nonvolatile memory 82 in order to control the position of the valve 41 between the first "off" position and the second "on" position, or variably in between "on" and "off", depending on the ICP data from the pressure transducer 30 and through a valve driver control circuit communicating with the pressure transducer 30 and the valve 41.

It is understood that filtering techniques, e.g., moving average, low pass filter, exponential smoothing, etc., may be applied to the ICP data by the operating program 84 to remove outlier data and/or noise. Also, the filtering techniques may be used to attenuate or remove micro fluctuations or oscillations within the incoming ICP sensor signals, for example, when the patient coughs, sneezes or changes position, to prevent overtreatment.

Operation of the valve driver control circuit may proceed as described below. In a valve closed position mode, the valve 41 is in the first "off" position as shown in step 100. At step 102, the microcontroller 80 will receive the ICP data from the pressure transducer 30 for example through connector 45. It is understood that the microcontroller 80 may receive the ICP data that is at a sampling rate that is at least as high as ten times the heart rate. For example, the average heart rate for adults is 60 to 100 beats per minute so the pressure may be sampled at least 600 to 1000 times per minute (or about 10 to 17 times per second). It is understood that the ICP may be allowed to stabilize prior to obtaining the ICP reading. It is also understood that the ICP data may be averaged to provide an average ICP representing a period of time that is longer than the sampling rate thus eliminating the effects of micro fluctuations. For example, ICP data may be sampled 10 to 17 times per second but averaged to provide ICP representing an average ICP every 0.5 second or every second.

At step 104, the microcontroller 80 will determine if the ICP or average ICP is above the target range of the ICP and therefore is in the "high" range. The program may include an adjustable tolerance allowing for pressures that are slightly above or below the target range without intervention. For example, the medical professional may input a target range of 10 to 15 mmHg but an acceptable upper threshold would be 2 mmHg above the target range, e.g., 17 mmHg. The tolerance may be set between ±1 to 5 mmHg to allow for small pressure changes to occur without intervention.

At step 104, if a "high" ICP threshold is triggered, the microcontroller 80 will proceed to the delay protocol which requires the microcontroller 80 to wait for a predetermined amount of time (TD), e.g., between 1 and 10 seconds and between 1 and 5 second, and at least 2 seconds and at least 5 seconds, before adjustment of the valve 41 is permitted, as indicated by step 106.

Alternatively, at step 104, if the ICP or average ICP is within the acceptable range, the valve 41 will remain in the first "off" position and will continue to receive the ICP data from the pressure transducer 30 at the high sampling rate as indicated by previous steps 100 and 102.

Figure 6:
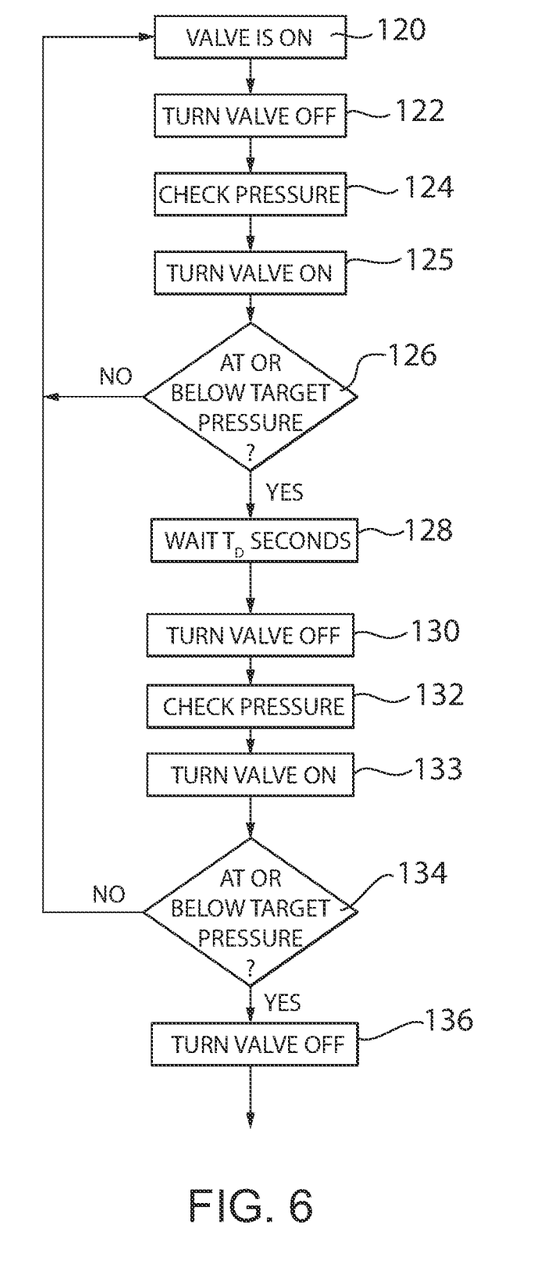
FIG. 6 is a flow diagram showing open valve operation of the flow controller of FIGS. 1 and 2 to accommodate for transient changes or fluctuations in intracranial pressure (ICP) caused by coughs or sneezes and to close the valve momentarily to check for ICP at a high sampling rate.

If the delay protocol is initiated, at step 108, after the predetermined delay time period (TD) has passed, the microcontroller 80 will again receive the ICP data from the pressure transducer 30. At step 110, if a "high" ICP threshold is still maintained, the microcontroller 80 will move the valve 41 to the second "on" position to start draining CSF through the flow controller 40 and relieve the elevated pressure in the brain as indicated by step 112. The microcontroller 80 will then proceed to valve open operating mode, as illustrated by FIG. 6. It is understood that the ICP data taken after the delay time period (TD) may represent an average ICP during the delay time period rather than an instantaneous ICP reading so that micro fluctuations are not considered.

Alternatively, at step 108, after the predetermined delay time has passed, if the ICP is at or below the acceptable range, the valve 41 will remain in the first "off" position, indicating that the high pressure fluctuation was transient, for example, as a result of a patient sneeze, cough or repositioning, and the valve 41 will remain closed to drainage as indicated by step 100.

Referring now to FIG. 6, in valve open operating mode, the valve 41 is in the second "on" position as shown in step 120. At step 122, the microcontroller 80 will turn the valve 41 to the first "off" position, and then receive ICP data from the pressure transducer 30 as shown in step 124. It is understood that the ICP may be allowed to stabilize prior to taking the ICP reading. The microcontroller 80 will then turn the valve 41 back to the second "on" position as shown in step 125. It is understood that the microcontroller 80 may receive the ICP data at a rate that is at least as high as ten times the heart rate. For example, the average heart rate for adults is 60 to 100 beats per minute so the pressure may be sampled at least 600 to 1000 times per minute (or approximately 10 to 17 times per second). It is also understood that the ICP data may be averaged to provide an average ICP representing a period of time that is longer than the sampling rate thus eliminating the effects of micro fluctuations. For example, ICP data may be sampled 10 to 17 times per second but averaged to provide ICP representing an average ICP every 0.5 second or every second.

At step 126, the microcontroller 80 will determine if the ICP or average ICP is at or below the acceptable range of the ICP, i.e., constituting "acceptable" or "low" ICP pressure. The program may include an adjustable tolerance allowing for pressures that are slightly above or below the target range without intervention. For example, the medical professional may input a target range of 10 to 15 mmHg but an acceptable upper threshold would be 2 mmHg above the target range, e.g., 17 mmHg. The tolerance may be set between ±1 to 5 mmHg to allow for small changes to occur without intervention.

At step 126, if the ICP or average ICP drops to a level equal to or below the "high" pressure threshold, the microcontroller 80 will proceed to the delay protocol which requires the microcontroller 80 to wait for a predetermined amount of time (TD), e.g., between 1 and 10 seconds, and between 1 and 5 seconds, and at least 2 seconds and at least 5 seconds, before closing the valve 41 as indicated by step 128.

Alternatively, at step 126, if the ICP is above the "high" threshold, the valve 41 will remain at the second "on" position to continue draining CSF and relieving the elevated pressure in the brain as indicated by step 120.

If the delay protocol is initiated, at step 130, after the delay period (TD), the microcontroller 80 will turn the valve 41 to the first "off" position and then will receive the ICP data from the pressure transducer 30 as indicated by step 132. The microcontroller 80 will then turn the valve 41 back to the second "on" position as shown in step 133.

At step 134, the microcontroller 80 will again determine if the ICP or average ICP is at or below the acceptable range of the ICP, i.e., constituting "acceptable" or "low" ICP pressure. It is understood that the ICP data during the delay time period (TD) may represent an average ICP during the delay time period rather than an instantaneous ICP reading so that micro fluctuations are not considered.

At step 134, if the pressure is maintained in the "low" range after the delay period, the microcontroller 80 will move the valve 41 to the first "off" position to stop draining CSF through the flow controller 40 and to prevent over drainage as indicated by step 136. The microcontroller 80 then proceeds to run the operating program 84 which relates to valve closed position mode, as previously illustrated and described with respect to FIG. 5.

Alternatively, at step 134, if the ICP or average ICP is in the "high" range, the valve 41 will remain at the second "on" position, indicating that the pressure drop was transient, for example, because of a patient repositioning, and the valve 41 will remain open in order to continue necessary draining of CSF as indicated by step 120.

The operation of the valve driver control circuit to open or close the valve 41 based on large changes in ICP and the continuous sampling of ICP by closing the valve 41 regardless of ICP level will continue as needed in an automated manner in order to eliminate the need for the nurse to continuously monitor drainage and re-level the patient's head level.

Figure 7:
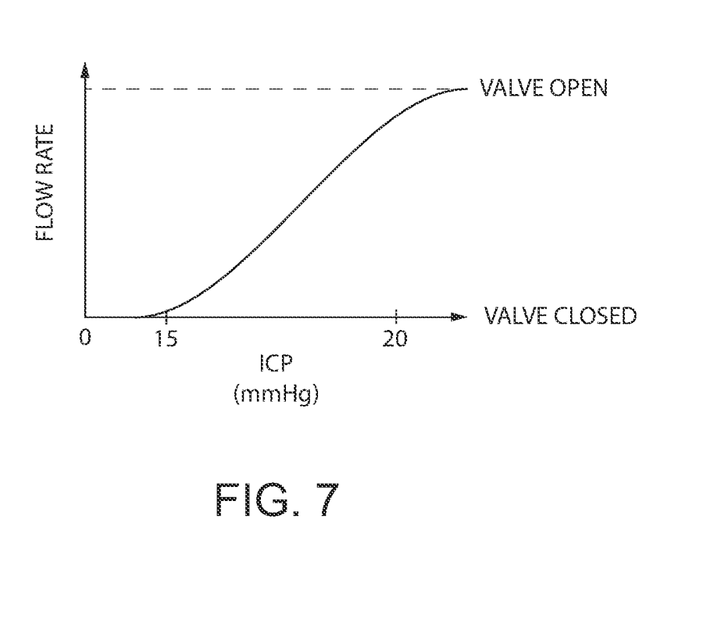
FIG. 7 is a graph showing control of flow rates through the valve of FIGS. 1 and 2 based on detected trends in ICP.

Referring now to FIG. 7, in an alternative embodiment of the present invention, the microcontroller 80 may regulate the flow rate of CSF through the flow controller 40 depending on the ICP data received from the pressure transducer 30. For example, the microcontroller 80 may consider trends in pressure changes to anticipate future events in pressure changes.

If a trend of increasing ICP is detected, the flow rate of CSF through the flow controller 40 may also be increased at an increasing or exponential rate to a steady state flow rate consistent with a fully open valve 41. In this respect, if it is detected that the ICP is increasing or monotonically approaching an elevated pressure level (e.g., pressure is in the 15 to 20 mmHg range), the valve 41 may begin anticipatory drainage of the ICP through the valve 41 at an exponentially increasing rate such as to anticipate high pressure build up and thus draining the CSF before the ICP reaches the high pressure level threshold (e.g., 20 mmHg) that requires fully open valve drainage. It is understood that the system may consider trends in the average ICP taken by averaging the ICP over short periods of time in order to eliminate the influence of micro fluctuations.

If a trend of decreasing ICP is detected, the flow rate of CSF through the flow controller 40 may also be decreased at a decreasing or exponentially decreasing rate to a zero flow rate consistent with a fully closed valve 41. In this respect, if it is detected that the ICP is approaching a normal or low pressure level (e.g., pressure is between 15 to 20 mmHg), the valve 41 may begin closing the valve 41 at an exponentially increasing rate such as to anticipate the pressure reaching normal levels (e.g., 10 to 15 mmHg) and no longer needing drainage. Over drainage may result in clogs or blockages in the catheter. It is understood that the system may consider trends in the average ICP taken by averaging the ICP over short periods of time in order to eliminate the influence of micro fluctuations.

Figure 8:
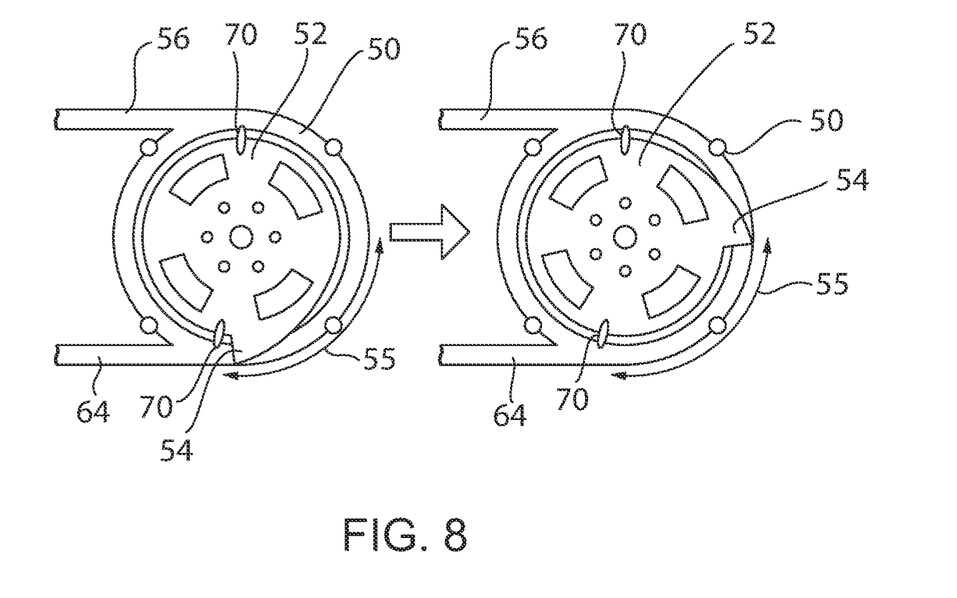
FIG. 8 is an alternative embodiment of the flow controller of FIG. 2 providing a rotating guide rotating a roller with increasing extension to compress the EVD tubing at varying degrees to change the size of the opening in the EVD tubing and thus to change the flow rates according to the graph of FIG. 5.

Referring also to FIG. 8, the flow controller 40 of FIG. 2 may be adapted to allow for gradual flow rate changes proportional to a cross sectional area of the medical tubing 22 at the compression point of the valve 41, and therefore, providing variable flow rates through the valve 41 according to the flow operation described with respect to FIG. 7.

In one embodiment of the present invention, the valve 41 may include a roller 54 with increasing outward extension into the circular channel 50 or an inclined or curved surface so that the degree of compression of the medical tubing 22 increases along a length of the roller 54. As the roller 54 rotates 90 degrees counterclockwise along the circular channel 50 as indicated by arrow 55, and similar to operation of FIG. 2, the roller 54 will begin compressing the medical tubing 22 to an increasing degree until the greatest extension point of the roller 54 fully pinches the medical tubing 22 to close the tube opening. As the roller 54 rotates 90 degrees clockwise along the circular channel 50 as indicated by arrow 55, the roller 54 will begin releasing the compression of the medical tubing 22 until it is fully open.

Other types of valves, e.g., stopcocks, tube crimps, linear actuators, magnetic actuators, and the like, may be used to provide variable flow rates through the valve as understood in the art.

Flow Rate Detection

Figure 9:
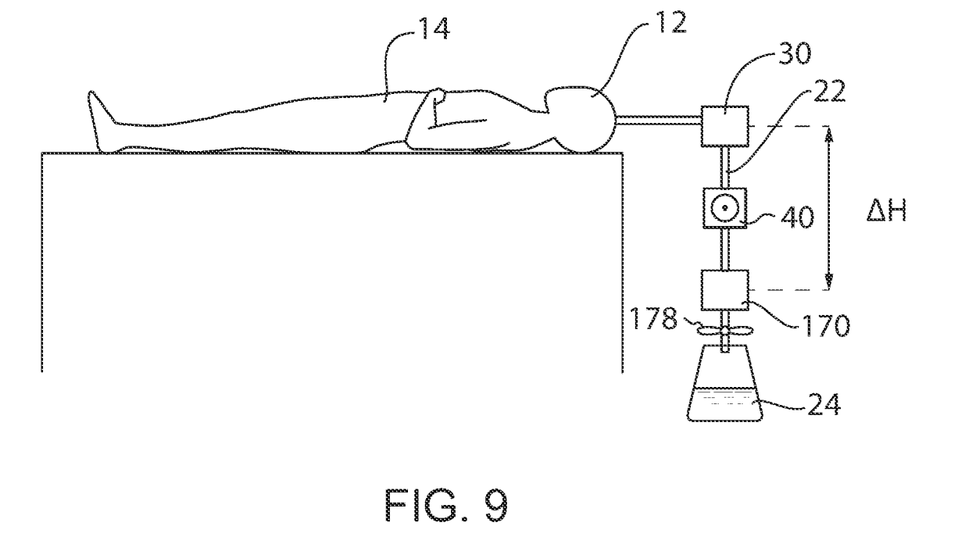
FIG. 9 is a schematic of the upstream pressure transducer installed at the patient's head and a downstream pressure transducer installed at the distal end of the EVD tubing to provide a flow rate detection method according to one embodiment of the present invention.

Referring to FIGS. 1 and 9, a downstream flow sensor may be a pressure transducer 170, similar to the upstream pressure transducer 30 described above, and may be installed on the medical tubing 22 downstream from the flow controller 40 in order to measure a flow rate of the CSF drainage. For example, the downstream pressure transducer 170 may measure the pressure drop of the fluid through the transducer which is proportional to the flow rate, and the transducer signal may be used to calculate flow rate.

In an alternative embodiment, the downstream flow sensor may be other fluid flow sensors known in the art, for example, turbine rotor or wheel flow meters, magnetic flow meters, ultrasonic flow meters, differential pressure flow meters, vortex shedding flow meters, and the like. It is understood that the flow sensor may be used to measure the flow rate of CSF drainage to allow the user to determine maximum flow rates and maximum drainage volumes and to determine when to stop or limit CSF drainage.

In one embodiment, the downstream flow sensor may be a wheel flow meter and may include a light-emitting diode (LED) and a sensor element interposed in the light path of the LED, perpendicular to the rotating wheel, and thus is able to detect the level of light from the LED indicating paddle movement of the rotating wheel. Paddle movement may also be detected magnetically, with each paddle or embedded piece of metal generating a pulse. As the fluid moves faster, more pulses are generated. A transmitter processes the pulse signal to determine the flow of the fluid. The wheel flow meter may be of the type sold by SP Industries, Inc./Bel-Art of Wayne, NJ under the commercial product name "Roto-Flo Pin Wheel Flow Indicator."

The downstream pressure transducer 170 may fluidly communicate with medical tubing 22 using a medical tubing 22 integrated with a non-compliant pressure tubing section 172 or using a short section of non-compliant pressure tubing section 172 attached to the medical tubing 22 using connectors 174, 176, for example, Luer locks. In the latter, a fourth portion of the medical tubing 22d is connected to a first connector 174 of the downstream pressure transducer 170 and a fifth portion of the medical tubing 22e may be attached to a second connector 176 to provide a leak proof union between the medical tubing 22 and the non-compliant pressure tubing section 172. The non-compliant pressure tubing section 172 may be used within the downstream pressure transducer 170 to ensure accuracy. The downstream pressure transducer 170 is generally positioned below the level of the flow controller 40 and above the level of the drainage bag 24.

The downstream pressure transducer 170 will convert an applied pressure of the CSF flow through the non-compliant pressure tubing section 172 into an electrical signal to provide pressure data indicative of a pressure at or near the drainage bag 24. The non-compliant pressure tubing section 172 deforms under the application of pressure caused by the CSF flow at or near the drainage bag 24 and this deformation is detected to provide a pressure reading representative of the pressure at or near the drainage bag 24.

The downstream pressure transducer 170 may be the same or similar to the upstream pressure transducer 30 and be of the type sold by ICU Medical of San Clemente, CA, under the commercial product name "Transpac IV Disposable Pressure Transducer."

The fifth portion of the medical tubing 22e may allow CSF to flow through a distal end 23 of the medical tubing 22 to a drainage bag 24 connected to the distal end 23 of the medical tubing 22. The drainage bag 24 will retain the CSF which can be emptied and replaced by the medical professional when full or when drainage is complete.

A stopcock 178 may be installed below the downstream pressure transducer 170 to allow for accurate pressure readings by the second downstream pressure transducer 170. The stopcock 178 may be closed to the "off" positioned in order to measure an accurate pressure at the downstream pressure transducer 170 (otherwise the drainage pressure will also be obtained). The stopcock 178 may be closed to the "off" position manually or automatically actuated by a controller as described above with respect to the operation of the valve of FIG. 2.

A height or vertical distance ($\Delta H$) between the upstream pressure transducer 30 and the downstream pressure transducer 170, in combination with the pressure data at the upstream pressure transducer 30 and the downstream pressure transducer 170, can be used to calculate a flow rate of the ICP. For example, Bernoulli's equation, $P + 1/2 \rho v^2 + \rho g h = C$, can be used to calculate flow rate though the flow controller 40. The calculated flow rate can be used by the microcontroller 80 in a closed loop system to monitor and control the flow rate of CSF through the flow controller 40.

In-Line High Pressure Detector

Figure 10:
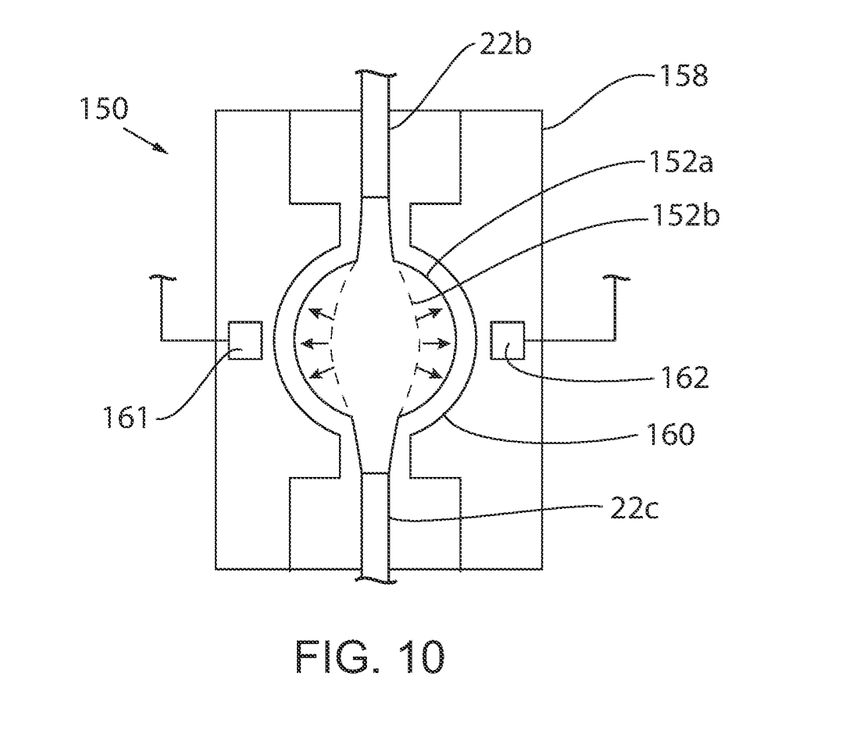
FIG. 10 is a collapsible chamber providing high pressure detection to the operation of the valve caused by over drainage of CSF in the brain according to one embodiment of the present invention.

Referring now to FIGS. 1 and 10, in one embodiment of the present invention, a high pressure detector 150 may be installed on the medical tubing 22 in order to detect greatly raised pressures, often to a critical level, or persistent ICP elevation indicating, e.g., severe brain swelling with limited CSF drainage. The high pressure detector 150 will fluidly communicate with the medical tubing 22 using a medical tubing 22 integrated with an inflatable bubble section 152 or using the inflatable bubble section 152 attached to the medical tubing 22 using connectors 154, 156, for example, Luer locks. In the latter, a second portion of the medical tubing 22b is connected to the first connector 154 of the inflatable bubble section 152 and a second portion of the medical tubing 22c may be attached to a second connector 156 to provide a leak proof union between the medical tubing 22 and the inflatable bubble section 152. The high pressure detector 150 is generally positioned at or below the level of the patient's ear (i.e., tragus).

The inflatable bubble section 152 may be a medical grade, low-density polyethylene, latex, polyether block amide, silicone, poly-siloxane, polyethylene terephthalate, nylon, and polyurethane, which provides high compliance and flexibility desired for high pressure sensing. The elasticity of the inflatable bubble section 152 material will allow the inflatable bubble section 152 to contract to a relatively smaller size (as shown by 152b) when there are low pressure levels of the CSF and expand to a larger size (as shown by 152a) at greatly raised (or critical) pressure levels of the CSF inflating the inflatable bubble section 152. In the expanded state, the inflatable bubble section 152a is a spherical ball shape like an inflated balloon. The inflation state of the inflatable bubble section 152 is proportional to the CSF pressure levels.

The inflatable bubble section 152 may be held within a bubble housing 158 providing a spherical cavity 160, holding the inflatable bubble section 152, and allowing the connectors 154, 156 to attach to the medical tubing 22. A first sensor element 161 may be held stationary by the bubble housing 158 at one end across a width of the inflatable bubble section 152 and a second sensor element 162 may held stationary by the bubble housing 158 at an opposite end across the width of the inflatable bubble section 152. The sensor elements 162, 164 may be positioned across the width of the inflatable bubble section 152, perpendicular to the extension of the medical tubing 22, in order to provide a signal when the sensors detect threshold physical changes such as expansion of the inflatable bubble section 152 when inflated by high pressures along the flow path.

In one embodiment, the first sensor elements 162 may be a light-emitting diode (LED) and the second sensor element 164 may be a photo-optic sensor interposed in the light path of the LED and able to detect the level of light from the LED. In this respect, the photo-optic sensor will detect changes in the light level from the LED and passing through the inflatable bubble section 152 as the inflatable bubble section 152 inflates or deflates depending on the pressure level within the inflatable bubble section 152.

It is understood that other noninvasive methods of detection may be used to detect changes in the size or diameter of the inflatable bubble section 152 along its width, for example, photoelectric sensors, capacitance sensors, and ultrasound sensors.

If the inflatable bubble section 152 is inflated by a predetermined amount, for example, between 10% to 50% and by at least 20% and at least 30% and at least 40% and at least 50% fully inflated or an increased diameter, a critical pressure signal may be sent to the flow controller 40 in order to immediately stop drainage of the CSF through the valve 41. In this respect, when a threshold critical pressure level is reached, greatly elevated pressures indicate that CSF may no longer being adequately drained though the medical tubing 22 and the greatly raised pressure is indicative of a condition such as swelling in the brain, not excess CSF.

It is understood that certain disposable elements of the present invention may be attachable to equipment commonly used with conventional EVD systems. For example, the medical tubing 22 may be sold with a pre-installed upstream pressure transducer 3, high pressure detector 150, downstream pressure transducer 170, and optionally, the drainage bag 24 in a kit assembly to be attachable to a flow controller 40, as taught by the present invention above, and a conventional bedside monitor 36 already at the patient's bedside. In this respect, the kit assembly may include elements that are lightweight, less expensive, and discarded after use and connectable to non-disposable components, such as the flow controller 40 and bedside monitor 36.

It is understood that the present invention may be applied to other fluid drainage or removal processes of the human body, for example, when there are excess fluids in the body caused by cancer, cirrhosis, infection, inflammation, injury, or other conditions. Common areas where the present invention may be applied to drainage processes include the lower legs, hands, abdomen and chest. The present invention provides flow sensing and flow control as described above during these other fluid removal processes.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

We claim:

1. A cerebrospinal fluid (CSF) drainage system used to treat an abnormal accumulation of CSF in a brain or spinal cord of a patient, comprising:
   a medical tubing connectable to a catheter implanted within the brain or spinal cord of the patient with a proximal portion of the catheter within the brain or spinal cord opposite a distal portion of the catheter attachable to the medical tubing and configured to divert CSF out of the brain or spinal cord to the medical tubing;
   a pressure sensor communicating with the medical tubing and configured to produce a pressure signal representing an intracranial pressure;
   a flow controller communicating with the medical tubing to conduct excess CSF through the medical tubing in a first state and to prevent the excess CSF from passing through the medical tubing in a second state;
   an elastic balloon positioned between the brain or spinal cord of the patient and the flow controller to accumulate CSF by elastically changing volume; and
   a driver control circuit communicating with the pressure sensor and the flow controller and operating to control the flow of excess CSF from the elastic balloon as a continuous function of the pressure signal within a pressure range.

2. The system of claim 1 wherein the pressure signal is obtained by values of intracranial pressure above a predetermined threshold for a predetermined duration of at least 2 seconds.

3. The system of claim 2 wherein the pressure signal is average intracranial pressure over the predetermined time duration.

4. The system of claim 2 wherein the predetermined duration is between 2 and 5 seconds.

5. The system of claim 1 wherein the driver control circuit is configured to regulate a flow controller at multiple points in a range of flow rates between on and off.

6. The system of claim 5 wherein a flow rate of CSF through the medical tubing is adjusted by changing a cross-sectional area of the medical tubing.

7. The system of claim 6 wherein the flow controller is a pinch valve pinching an outer surface of the medical tubing.

8. The system of claim 7 wherein the pinch valve is a roller rollable along the medical tube to compress the medical tubing.

9. The system of claim 8 wherein the roller compresses the medical tubing in a first position and decompresses the medical tubing in a second position wherein the first and second positions are approximately 90 degrees apart.

10. The system of claim 8 wherein the pinch valve further comprises a position sensor detecting a position of the roller between the first position and the second position.

11. The system of claim 8 wherein the pinch valve further comprises stop blocks preventing rotation of the roller beyond the 90-degree rotation.

12. The system of claim 1 further comprising a second pressure sensor connected to the medical tubing downstream from the flow controller.

13. The system of claim 1 further comprising a photo sensor detecting a change in light level as the elastic balloon expands indicating the volume within the expandible chamber.

14. A method of treating an abnormal accumulation of cerebrospinal fluid (CSF) comprising the steps of:
   connecting a proximal end of medical tubing to a catheter implanted within the brain or spinal cord of the patient opposite a distal portion of the catheter attachable to the medical tubing and diverting CSF out of the brain or spinal cord to the medical tubing, the medical tube being connected to
   a pressure sensor producing a pressure signal representing an intracranial pressure;
   a flow controller in line with the pressure sensor to conduct excess CSF to drain out of the brain or spinal cord through the medical tubing in a first state and to prevent the excess CSF from passing out of the brain or spinal cord through the medical tubing in a second state;
   an elastic balloon positioned between the brain or spinal cord of the patient and the flow controller to accumulate CSF by elastically changing volume; and
   a driver control circuit communicating with the pressure sensor and the flow controller;
   (a) operating the driver control circuit to control a flow of excess CSF from the elastic balloon as a continuous function of the pressure signal within a pressure range:
   (b) draining CSF from the brain or spinal cord through the medical tubing to a drainage bag.

15. The method of claim 14 wherein the step of controlling the flow of excess CSF controls the flow of CSF depending on a pressure trend such that if the pressure trend is increasing, the flow of CSF is increased, and if the pressure trend is decreasing, the flow of CSF is decreased.

16. The cerebrospinal fluid (CSF) drainage system of claim 1 wherein the driver control circuit further controls the flow of excess CSF from the elastic balloon according to a pressure trend derived from the pressure sensor such that if the pressure trend is increasing the flow of CSF is increased and if the pressure trend is decreasing the flow of CSF is decreased.

* * * * *